United States Patent [19]

Fahmy

[11] Patent Number: 4,457,923

[45] Date of Patent: Jul. 3, 1984

[54] O-TRIHALOETHYL PHOSPHORODITHIOATE PESTICIDES

[75] Inventor: Mohamed A. H. Fahmy, Princeton, N.J.

[73] Assignee: FMC Corporation, Philadelphia, Pa.

[21] Appl. No.: 364,130

[22] Filed: Mar. 31, 1982

[51] Int. Cl.³ .................... A01N 57/12; C07F 9/165
[52] U.S. Cl. ................................. 424/224; 260/955; 260/963
[58] Field of Search ................ 260/955, 963; 424/224

[56] References Cited

U.S. PATENT DOCUMENTS

| | | | |
|---|---|---|---|
| 3,112,244 | 11/1963 | Goyette | 260/963 |
| 3,499,951 | 3/1970 | Schrader et al. | 260/955 |
| 4,190,653 | 2/1980 | Saito et al. | 260/955 |
| 4,235,891 | 11/1980 | Saito et al. | 260/955 |

FOREIGN PATENT DOCUMENTS 123096 11/1976 German Democratic Rep. ................................. 260/963

Primary Examiner—Anton H. Sutto
Attorney, Agent, or Firm—Robert L. Andersen; H. Robinson Ertelt

[57] ABSTRACT

Compounds of the formula

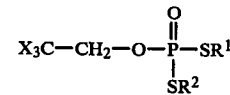

in which X is halogen and $R^1$ and $R^2$ are each alkyl groups, insecticidal, acaricidal and nematicidal compositions thereof, and a method for controlling such pests are disclosed.

9 Claims, No Drawings

O-TRIHALOETHYL PHOSPHORODITHIOATE PESTICIDES

The present invention relates to a new class of insecticides, namely O-trihaloethyl phosphorodithioates, to insecticidal compositions thereof, and to a method for control of nematodes and insects.

The compounds of this invention are O-trihaloethyl phosphorodithioates of the formula:

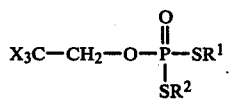
$$X_3C-CH_2-O-\overset{\overset{O}{\|}}{\underset{SR^2}{P}}-SR^1 \qquad I$$

in which X is a halogen such as chlorine, bromine or fluorine and $R^1$ and $R^2$ are each alkyl of 1 to 6 carbon atoms, straight or branched chain. In one embodiment the invention comprises a compound of formula I in which X is fluorine; in another, the compound in which X is chlorine. In either or both of these embodiments $R^1$ and $R^2$ may be as defined above, or one of $R^1$ and $R^2$ may be straight or branched chain alkyl of 3 to 4 carbon atoms and the other of $R^1$ and $R^2$ may be straight or branched chain alkyl of 2 to 4 carbon atoms.

With reference to formula I the following compounds may be specifically mentioned:

| Compound No. | X | $R^1$ | $R^2$ |
| --- | --- | --- | --- |
| 1 | F | propyl | ethyl |
| 2 | F | isopropyl | ethyl |
| 3 | F | isopropyl | propyl |
| 4 | F | isopropyl | isopropyl |
| 5 | F | butyl | ethyl |
| 6 | F | butyl | propyl |
| 7 | F | butyl | isopropyl |
| 8 | F | sec-butyl | ethyl |
| 9 | F | sec-butyl | propyl |
| 10 | F | sec-butyl | isopropyl |
| 11 | F | sec-butyl | butyl |
| 12 | F | tert-butyl | ethyl |
| 13 | F | tert-butyl | propyl |
| 14 | F | tert-butyl | isopropyl |
| 15 | F | tert-butyl | sec-butyl |
| 16 | F | tert-butyl | tert-butyl |
| 17 | Cl | sec-butyl | sec-butyl |

It will be apparent from the foregoing that within the scope of the invention other alkyl groups, for example methyl, iso-butyl, straight or branched chain or cyclic pentyl or hexyl, may be substituted for the $R^1$ and/or $R^2$ groups shown above.

The following examples illustrate preparation of the compounds of this invention.

EXAMPLE 1

Synthesis of O-(2,2,2-Trifluoroethyl) S-sec-butyl S-propyl phosphorodithioate

Step A: Synthesis of S-sec-butyl phosphorothioic dichloride To a solution of 90.2 g (1.0 mole) of 1-methyl-1-propanethiol in 300 ml of toluene, maintained between −3° C. and 7° C., 148 g (1.1 mole) of sulfuryl chloride was added dropwise during a one hour period. To this mixture, at −3° C., 60 g (1.0 mole) of glacial acetic acid was added in one portion. The dropwise addition of 137.3 g (1.0 mole) of phosphorous trichloride at −3° C. to 6° C. followed during a one hour period. The reaction mixture was then stirred at room temperature for approximately sixteen hours. After adding 3 ml of sulfuryl chloride the solvent was removed using a rotary evaporator under vacuum. The brown oil that remained was vacuum distilled, yielding 168.9 g of S-sec-butyl phosphorothioic dichloride, b.p. 75° C./1.8 mm of Hg. An nmr spectrum of the product was consistent with the assigned structure.

Step B: Synthesis of O-(2,2,2-trifluoroethyl) S-sec-butyl phosphorothioic chloride To a solution of 51.8 g (0.25 mole) of S-sec-butyl phosphorothioic dichloride (Step A product) in 150 ml of toluene cooled to 0° C. in an ice bath 29 g (0.29 mole) of 2,2,2-trifluoroethanol was added dropwise, followed by the dropwise addition of 19.8 g (0.25 mole) of pyridine. The reaction mixture was allowed to warm to ambient temperature and was stirred overnight. The mixture was filtered, and the solvent was evaporated from the filtrate, leaving a colorless oil. This oil was distilled in a short path distillation apparatus. A single fraction weighing 52.7 g, b.p. 61–68° C./0.1 mm Hg., was collected. Analysis by nmr indicated a purity of 80% O-(2,2,2-trifluoroethyl) S-sec-butyl phosphorothioic chloride. The major contaminant was O,O-di-(2,2,2-trifluoroethyl) S-sec-butyl phosphorothioate. Further purification failed to separate the major components, making it necessary in Step C to use product as originally isolated.

Step C: Synthesis of O-(2,2,2-trifluoroethyl) S-sec-butyl S-propyl phosphorodithioate To a suspension of 0.6 g (0.025 mole) of sodium hydride in 50 ml of tetrahydrofuran, at 50° C. under a nitrogen atmosphere, was added dropwise 2.0 g (0.026 mole) of 1-propanethiol. The mixture was stirred until hydrogen evolution ceased. It was then poured into a solution of 9.5 g (0.035 mole) of O-(2,2,2-trifluoroethyl) S-sec-butyl phosphorothioic chloride (Step B product) in 25 ml of tetrahydrofuran. This mixture was stirred at room temperature overnight. The solvent was evaporated under reduced pressure, and the residue was dissolved in 50 ml of toluene. This solution was washed twice with 25 ml of water, dried over anhydrous sodium sulfate, and filtered. The toluene was evaporated under reduced pressure, leaving 9.46 g of an orange oil. This procedure was repeated, yielding 9.1 g of orange oil. These oils were combined and were distilled under vacuum, yielding the following fractions:

1. 3.5 g, b.p. 71°–82° C./0.03 mm of Hg
2. 1.26 g, b.p. 82°–94° C./0.03 mm of Hg
3. 8.35 g, b.p. 94°–98° C./0.03 mm of Hg

The nmr spectrum of fraction 3 was consistent with the assigned structure, O-(2,2,2-trifluoroethyl) S-sec-butyl S-propyl phosphorodithioate, and showed this product to be 95% pure.

EXAMPLE 2

Synthesis of O-(2,2,2-Trichloroethyl) S,S-di-sec-butyl phosphorodithioate

Step A: Synthesis of O-(2,2,2-trichloroethyl) phosphoric dichloride

A solution of 52.3 g (0.35 mole) of 2,2,2-trichloroethanol and 53.7 g (0.35 mole) of phosphorous oxychloride in 150 ml of toluene was cooled to −10° C. To this solution, under nitrogen, 27.7 g (0.35 mole) of pyridine was added dropwise while maintaining the temperature at −10° C. Upon completion of addition the temperature was allowed to rise to ambient conditions, and the mixture was stirred overnight. The solid was filtered from the reaction mixture and the toluene evaporated under vacuum. The liquid residue was distilled, yielding the following fractions:

1. b.p. 68°–70° C./0.05 mm of Hg
2. b.p. 73°–75° C./0.05 mm of Hg

Combined weight of the fractions was 51.5 g. Analysis showed that both were O-(2,2,2-trichloroethyl) phosphoroic dichloride, fraction 2 being slightly more pure than fraction 1.

Step B: Synthesis of O-(2,2,2-trichloroethyl) S,S-di-sec-butyl phosphorodithioate To a suspension of 0.92 g (0.04 mole) of sodium hydride in dry tetrahydrofuran under a nitrogen atmosphere was added dropwise 3.61 g (0.04 mole) of 1-methyl-1-propanethiol. Upon completion of addition the mixture was stirred for two hours after which 5.32 g (0.02 mole) of O-(2,2,2-trichloroethyl) phosphoroic dichloride (Step A product) was added in one portion. The reaction was stirred overnight. The solvent was evaporated under a vacuum, and 100 ml of toluene was added to the reaction mixture. This solution was washed three times with water, dried over anhydrous sodium sulfate, filtered, and the solvent evaporated under vacuum. The product, O-(2,2,2-trichloroethyl) S,S-di-sec-butyl phosphorodithioate, was subjected to high vacuum to remove volatile impurities. The product weighed 4.31 g. Both proton and phosphorous nmr spectra agreed with the assigned structure.

The compounds of this invention control nematodes, insects, including soil borne insects such as corn rootworm and insects which feed on the above ground portions of the plant such as aphids, and mites. For nematode and corn rootworm control the compound is advantageously applied to or incorporated into the soil in which crops are planted or are to be planted, or to the plant's roots. If it is desired to control only pests attacking the above ground portions of the plant the compound may suitably be applied to the above ground portion of the plant.

The compounds are generally not applied full strength but are typically applied as formulations which may be applied as such or further diluted for application. Typical formulations include compositions of the active ingredient in combination with one or more agriculturally acceptable adjuvants, carriers or extenders, preferably with a surface active agent, and optionally with other active ingredients. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of active ingredient depending upon the particular agent used, the additives and carriers used, other active ingredients, and the desired mode of application.

With due consideration to these factors the active ingredient of a typical formulation may, for example, be suitably present at a concentration of about 0.01% up to about 95%, preferably 0.1% up to 90%, of the formulation, agriculturally acceptable carriers, diluents, adjuvants, and other suitable active ingredients comprising the balance of the formulation. Compatible surface active agents, if employed in a formulation, may be present at various concentrations, suitably in the range of 1 to 30% by weight of the formulation.

The formulation may be used as such or diluted to a desired use dilution with a diluent or carrier suitable for facilitating dispersion of the active ingredients. A suitable concentration of the active ingredient in the use dilution may be in the range of 0.005% to 10%, more preferably 0.01% to about 10%, by weight.

Many variations of spraying, dusting, and controlled or slow release compositions of a type known in the art may be used by substituting or adding an insecticidal compound or compounds of this invention into the compositions known or apparent to the art.

The insecticidal compounds of this invention may be formulated and applied with other compatible active agents including nematicides, insecticides, acaracides, fungicides, plant regulators, herbicides, fertilizers, and the like.

In applying these compounds, whether alone or with other agricultural chemicals, an effective insecticidal, acaricidal or nematicidal amount of the active ingredient must be applied. While the application rate will vary widely depending on the choice of compound, formulation, mode of application, plant species being protected, planting density, and other like factors, a suitable use rate for agricultural crops may be in the range of 0.005 to 3 kg/ha, preferably 0.01 to about 1 kg/ha.

The compounds of this invention were tested for insecticidal activity as described below.

Insect Topical Application Test:

The test compound was dissolved in acetone and the resulting solution diluted with water to provide a test solution containing 500 nanograms/microliter. A 1 microliter droplet was applied to the second or third dorsal thoracic segment of each test larva. The insect was observed 24 hours later for toxic effect elicited by the test compound. An insect was considered dead if it could no longer right itself and move in an oriented pattern. The percent mortality for the test compounds against southern corn rootworm is reported in Table 1.

Soil Incorporation Tests for Residual Southern Corn Rootworm Control

A solution of the test compound, containing 335 ppm test compound in 100 ml of a solution containing 90% water, 9.75% acetone and 0.25% octylphenoxypolyethoxyethanol, was stirred into topsoil in an amount sufficient to provide the desired concentration. The container for the test sample was capped and stored for the desired storage period (14 to 42 days). At the end of the storage period each test sample was infested with 10 larvae and a kernel of germinating corn as a food supply. The samples were then recapped and returned to storage for three days at which time the tests were read for percent mortality.

The soil samples varied from test to test. In some tests there was employed a "synthetic soil" containing 1 part topsoil, one and one-half parts sand; and one and one-half parts vermiculite. In other tests, various types of topsoil were employed. For purposes of the present tests no attempt was made to distinguish between soil types.

The residual activity of the compounds of this invention is reported in Table I. The compounds of the invention showed excellent residual activity against the Corn Rootworm.

Soil Incorporation Tests for Nematode Control and Phytotoxicity

Each compound was tested for nematicidal activity as a formulated material. The formulation used was a 5 wt. % dust formulation made up as follows:
Active ingredient (100% active basis)—5 parts
Base—95 parts
96%—attaclay
2%—highly purified sodium lignosulfonate (100%)
2%—powdered sodium alkylnaphthalenesulfonate (75%)
The mixture was ground to a fine powder.

The formulation described above was tested for activity against root-knot nematode (*Meloidogyne incognita*) as follows:

Samples of infested soil were processed for nematodes by using the Caveness and Jensen centrifugal-sugar flotation extraction technique [Caveness, F. E. and Jensen, H. J., "Modification of the Centrifugal Flotation Technique for the Isolation and Concentration of Nematodes and their Eggs from Soil and Plant Tissue," Proc. Helm. Soc., Washington, 22, 87–89 (1955).] A 500 mesh sieve was used to collect the nematode larvae and eggs, and their number was estimated under a stereomicroscope.

Soil containing eggs and larvae was mixed with sufficient steam-sterilized sandy soil so that there were 800 to 1000 root-knot nematode larvae and eggs per pot of soil (three inch diameter each, containing approximately 300 g soil).

Soil so infested was used for soil incorporated nematicidal studies within two days of preparation. The formulated compounds to be tested for nematicidal activity were incorporated in the root-knot nematode infested potting soil to give soil treatment at several application rates in the range of 2.5 to 25 ppm (weight chemical/weight nematode infested soil). Young tomato plants were planted in this soil in three inch pots. At the end of two weeks the roots of all plants were examined and rated in comparison to untreated checks.

Control Treatments—The untreated check plants were treated in the same manner as those treated with the active ingredient.

The rating system and the results of the tests against root-knot nematode are shown in Table II. High levels of activity in the soil incorporated test were exhibited by most of the exemplified compounds; a low level of phytotoxicity was observed.

Similar tests were run against stunt nematode and lesion nematode at 15 ppm. The results are reported in Table III.

Evaluation of compositions of the invention against stunt nematode (*Tylenchorhynchus claytoni*) was carried out by incorporating the formulated active ingredient in soil in which a corn seedling was then planted, and two days thereafter inoculating the soil with stunt nematodes in mixed stages of growth, from larvae to adults. The soil was processed for nematode counting approximately five weeks after treatment. Untreated check plants showed no nematode control. Results with formulations of the invention are recorded in Table III as "Percent Control" relative to nematode control in the untreated check pot. The compositions tested showed control ranging from 16.2% to 92.2%.

Compositions were also evaluated against lesion nematode (*Pratylenchus penetrans*), following a similar procedure in which pea seedlings were planted instead of corn seedlings, and nematodes were extracted from the root systems, instead of from the soil. Untreated plants showed no nematode control. Results with formulations of the invention are recorded in Table III as percent control relative to nematode control in the untreated check pot. Most of the compositions tested showed control in the range of 70.8% to 99.1%.

Various modifications may be made in the formulation and application of the novel compositions of this invention without departing from the inventive concept herein, as defined in the claims below.

TABLE I

RESULTS OF INSECTICIDAL TESTING AGAINST THE SOUTHERN CORN ROOTWORM[a]

| | Percent Mortality | | | | |
| | | Initial | Residual Soil | | |
| Compound | Topical 500 ng/insect | Soil 10.0 ppm | 14 days 10.0 ppm | 21 days | 42 days |
|---|---|---|---|---|---|
| 1 | 100 | | | | |
| 2 | 80 | 100 | 70 | 100[b] | 100[c] |
| 3 | 100 | 100 | 75 | | |
| 5 | 0 | | | | |
| 6 | 100 | 100 | 60 | 100[b] | 100[b] |
| 7 | 0 | | | | |
| 8 | 100 | 100 | 40 | | |
| 9 | 100 | 100 | 70 | 100[b] | 100[d] |
| 10 | 100 | 100 | 90 | 25 | 100[e] |
| 11 | 100 | 100 | 50 | 40 | 100[d] | 100[b] |
| 12 | 40 | 85[f] | 65[f] | 100[g] | 100[h] |
| 13 | 0 | | | | |
| 14 | 0 | | | | |
| 15 | 20 | | | | |
| 16 | 0 | | | | |
| 17 | 0 | | | | |

[a]*Diabrotica undecimpunctata howardi* Barber;
[b]at 2.50 ppm;
[c]at 5.00 ppm;
[d]at 1.20 ppm;
[e]at 2.00 ppm;
[f]Average of two tests;
[g]at 20.00 ppm;
[h]at 40.00 ppm;

TABLE II

RESULTS OF NEMATICIDE TESTING AGAINST THE ROOT-KNOT NEMATODE[a]

| | Root Knot Index[b] | | | | Plant Injury Rating[e] |
| Compound | 25 ppm[c] | 10 ppm[c] | 5 ppm[d] | 2.5 ppm[d] | |
|---|---|---|---|---|---|
| 1 | 1.5 | 3 | 4 | 4 | 1 |
| 2 | 0.58 | 0.93 | 0.65 | 1.5 | 1 |
| 3 | 0.45 | 0.9 | 1.5 | 3 | 1 |
| 5 | 0 | 0.94 | 1.67 | 2.33 | 1 |
| 6 | 0 | 1.5 | 3.5 | 4 | 1 |
| 7 | 0.59 | 0.75 | 3 | 4 | 1 |
| 8 | 0.45 | 3.25 | 4 | 4 | 1 |
| 9 | 0 | 0 | 0.5 | 1.5 | 1 |
| 10 | 0.50 | 1.75 | 3.5 | 4 | 1 |
| 11 | 0 | 0.75 | 2.5 | 4 | 1 |
| 12 | 0.75 | 2.25 | 4 | 4 | 1 |
| 13 | 0.25 | 2.6 | 4 | 4 | 1 |
| 14 | 3[d] | | | | 0 |
| 15 | 0.62 | 0.85 | 2.33 | 4 | 1 |

TABLE II-continued
RESULTS OF NEMATICIDE TESTING AGAINST THE ROOT-KNOT NEMATODE[a]

| Compound | Root Knot Index[b] 25 ppm[c] | 10 ppm[c] | 5 ppm[d] | 2.5 ppm[d] | Plant Injury Rating[e] |
|---|---|---|---|---|---|
| 17 | 0[d] | | | | 0 |

[a]*Meloidogyne incognita*
[b]Knot Index
4 = no control
3 = 25% control
2 = 50% control
1 = 75% control
0.8 = 80% control
0.5 = 90% control
0.1–0.4 = 95–99% control
0 = complete control
[c]Average of two results
[d]One test
[e]Plant Injury Rating
0 = no injury
1 = slight phytotoxicity
2 = moderate phytotoxicity
3 = severe phytotoxicity
4 = plant not expected to survive

TABLE III
RESULTS OF NEMATICIDE TESTING AGAINST STUNT AND LESION NEMATODES

| Compound | Percent Control[a] Stunt[b] Nematode | Lesion[c] Nematode | Plant Injury Rating[d] |
|---|---|---|---|
| 2 | 39.7 | 93.6 | 1 |
| 3 | 54.3 | 99.1 | 1 |
| 5 | 76.3 | 3.9 | 1 |
| 6 | 54.7 | 93.3 | 1 |
| 7 | 63.6 | 37.3 | 1 |
| 8 | 39.9 | 87.3 | 1 |
| 9 | 92.2 | 98.2 | 1 |
| 10 | 69.0 | 92.2 | 1 |
| 11 | 82.6 | 98.5 | 1 |
| 12 | 16.2 | 70.8 | 1 |
| 13 | 57.1 | 71.0 | 1 |
| 15 | 85.8 | 92.1 | 1 |

[a]at 15 ppm
[b]*Tylenchorhynchus claytoni*
[c]*Pratylenchus penetrans*
[d]Plant Injury Rating
0 = no injury
1 = slight phytotoxicity
2 = moderate phytotoxicity
3 = severe phytotoxicity
4 = plant not expected to survive

I claim:

1. A compound of the formula

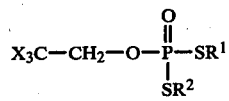

in which X is chlorine, bromine, or fluorine, $R^1$ and $R^2$ are each independently selected from alkyl of 1 to 6 carbon atoms, straight or branched chain.

2. The compound of claim 1 in which each X is fluorine.

3. The compound of claim 2 in which $R^1$ is alkyl of 3 to 4 carbon atoms and $R^2$ is alkyl of 2 to 4 carbon atoms.

4. The compound of claim 3 in which $R^1$ is isopropyl and $R^2$ is ethyl.

5. The compound of claim 3 in which $R^1$ is sec-butyl and $R^2$ is propyl.

6. The compound of claim 1 in which each X is chlorine.

7. An insecticidal composition comprising an insecticidal concentration of a compound of claim 1, 2, 3, 4, 5, or 6 in admixture with a compatible agriculturally acceptable carrier, diluent or adjuvant.

8. A method for controlling insects which comprises applying to the insect, to plants to which insects are attracted or upon which insects feed, or to soil in which such plants are planted an insecticidal amount of the compound of claim 1, 2, 3, 4, 5, or 6.

9. A method for controlling nematodes which comprises applying to the soil in which plants are or are to be planted a nematicidal amount of the compound of claim 1, 2, 3, 4, 5, or 6.

* * * * *